US012447088B2

(12) United States Patent
Abboud et al.

(10) Patent No.: US 12,447,088 B2
(45) Date of Patent: Oct. 21, 2025

(54) DEVICE AND METHOD FOR POSITIONING A JOINT

(71) Applicant: Trice Medical, Inc., Malvern, PA (US)

(72) Inventors: Joseph A. Abboud, Malvern, PA (US); Alfred J. Intintoli, West Chester, PA (US); Benjamin R. Brozanski, Philadelphia, PA (US)

(73) Assignee: Trice Medical, Inc., Malvern, PA (US)

( * ) Notice: Subject to any disclaimer, the term of this patent is extended or adjusted under 35 U.S.C. 154(b) by 834 days.

(21) Appl. No.: 17/065,854

(22) Filed: Oct. 8, 2020

(65) Prior Publication Data

US 2021/0113408 A1 Apr. 22, 2021

Related U.S. Application Data

(60) Provisional application No. 62/923,169, filed on Oct. 18, 2019.

(51) Int. Cl.

| | |
|---|---|
| ***A61G 15/00*** | (2006.01) |
| ***A61B 17/34*** | (2006.01) |
| ***A61G 15/12*** | (2006.01) |

(52) U.S. Cl.

CPC .......... *A61G 15/12* (2013.01); *A61B 17/3478* (2013.01); *A61G 15/002* (2013.01);

(Continued)

(58) Field of Classification Search

CPC .... A61G 15/12; A61G 15/002; A61G 13/122; A61G 13/1235; A61G 13/124;

(Continued)

(56) References Cited

U.S. PATENT DOCUMENTS

| | | | | |
|---|---|---|---|---|
| 1,891,755 A * | 12/1932 | Davis | A61G 13/12 602/39 |
| 2,667,917 A * | 2/1954 | Dustin | B60N 2/787 244/122 R |

(Continued)

FOREIGN PATENT DOCUMENTS

| | | | |
|---|---|---|---|
| EP | 3 369 391 A1 | 9/2018 |
| GB | 2 268 052 A | 1/1994 |
| WO | WO 2020/068672 A1 | 4/2020 |

OTHER PUBLICATIONS

International Search Report and Written Opinion for International Application No. PCT/US2019/052441, dated Dec. 10, 2019 in 17 pages.

(Continued)

*Primary Examiner* — Adam Baker
(74) *Attorney, Agent, or Firm* — Knobbe, Martens, Olson & Bear LLP

(57) ABSTRACT

The present invention related to a joint positioning device for positioning a joint and methods for using such devices. The joint positioning device may comprise a patient support comprising a substantially flat surface, the patient support configured to be positioned proximate to a chair; a shoulder pole mounted to the patient support, the shoulder pole oriented substantially perpendicular to a substantially flat surface of the patient support; and a cylindrical shoulder pad mounted to the shoulder pole, the shoulder pad oriented substantially perpendicular to the shoulder pole. The joint positioning device may further comprise a vertical pillar, the vertical pillar oriented substantially perpendicular to the substantially flat surface of the patient support.

12 Claims, 10 Drawing Sheets

(52) U.S. Cl.
CPC ...... *A61G 2200/34* (2013.01); *A61G 2200/54* (2013.01); *A61G 2203/70* (2013.01); *A61G 2210/10* (2013.01)

(58) Field of Classification Search
CPC .............. A61G 13/1255; A61G 7/1086; A61G 13/0072; A61G 2200/54; A61G 2200/34; A61G 2203/70; A61F 5/026; A61F 5/042; A61F 5/05; A61F 5/3723; A61F 5/3761; A61F 5/3792; A61H 2003/0255; A61H 2003/0261; A61H 2003/0272; A61H 1/0218; A61H 1/0229; A61H 1/0281; A61B 1/317; A61B 5/022; A47C 16/005–04; A47C 7/425; A47C 7/546; A47C 7/543; A47C 7/541; A47C 7/54; B60N 2/75; B60N 2/753; B60N 2/763–797
USPC .......................................................... 128/845
See application file for complete search history.

(56) References Cited

U.S. PATENT DOCUMENTS 2,678,857 A 5/1954 Hans
2,732,269 A * 1/1956 astroff .................... A61G 13/12 5/648
3,280,831 A * 10/1966 Mccall Parker ..... A61H 3/0288 135/86
4,457,302 A 7/1984 Caspari et al.
4,549,540 A 10/1985 Caspari et al.
4,583,725 A 4/1986 Arnold
4,624,245 A 11/1986 Mullin et al.
4,766,892 A 8/1988 Kreitman
4,834,457 A * 5/1989 Head ...................... A47C 7/546 248/118
4,909,264 A * 3/1990 Wadsworth, III .. A61G 13/0063 128/877
5,056,535 A 10/1991 Bonnell
5,171,317 A 12/1992 Corcoran
5,226,439 A 7/1993 O'Keeffe et al.
5,289,603 A 3/1994 Kumagai
5,360,392 A 11/1994 McCoy
8,506,476 B1 8/2013 O'Mara, Jr.
9,314,390 B2 * 4/2016 Hernandez ................ B67B 7/16
9,480,341 B2 * 11/2016 DiPaolo ................. A47C 7/546
9,480,616 B2 11/2016 Kreuzer et al.
9,918,890 B2 3/2018 Kreuzer et al.
11,259,640 B2 * 3/2022 Tozeski .................. A61B 5/022
2010/0242177 A1 9/2010 Malcolm
2014/0130260 A1 5/2014 Kreuzer et al.
2017/0135891 A1 5/2017 Kettner et al.
2017/0280988 A1 * 10/2017 Barbato ................. A61B 1/317
2021/0205163 A1 7/2021 McMillan et al.

OTHER PUBLICATIONS

Ward et al., Basic Knee Arthroscopy Part I: Patient Positioning, Nov. 2013, Arthrosc Tech, 2(4): e497-e499 (Year: 2013).

* cited by examiner

DEVICE AND METHOD FOR POSITIONING A JOINT

CROSS-REFERENCE TO RELATED APPLICATIONS

This application claims priority under 35 USC 119(e) to U.S. Provisional Application No. 62/923,169, entitled DEVICE AND METHOD FOR POSITIONING A JOINT, filed Oct. 18, 2019; the disclosure of which is hereby incorporated by reference in its entirety.

BACKGROUND OF THE INVENTION

Field of the Invention

This application describes apparatuses, methods, and systems for the positioning of a patient for proper visualization and access of tissues for injection or treatment.

Description of the Related Art

Traditional therapeutic and diagnostic surgical procedures for pathologies located within the body can cause significant trauma to the intervening tissues and potentially the target tissue site. Such procedures often require a long incision, extensive muscle stripping, prolonged retraction of tissues, denervation and devascularization of tissue. Such procedures may require operating room time of several hours followed by several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for orthopedic applications due to the need for access to locations within the body and the danger of damage to vital intervening tissues. While developments in minimally invasive surgery are steps in the right direction, there remains a need for further development in minimally invasive surgical instruments and methods.

Treatment of internal tissue sites, such as the treatment of an orthopedic joint, often requires proper positioning for visualization of and access to the target internal tissues for imaging and injections. Currently in the field, it is often difficult for a surgeon to access specific areas of the anatomy and thus they often fail to visualize and diagnose completely. However, when a patient is properly positioned, a surgeon or doctor may be able to access specific areas of the anatomy for proper diagnosis. With proper positioning, typically tight or inaccessible tissue sites within the patient can be opened up for visualization and access. Additionally, orthopedic joints must be properly positioned and stabilized for access to the desired internal tissue site, for proper visualization of the desired internal tissue site and to prevent injury to the patient. Consequently, there is need for improved devices and methods for positioning of a patient to open up areas for visualization and access to an internal tissue site.

SUMMARY

Examples of the present disclosure relate to joint positioning devices, methods, and systems.

In some examples, a joint positioning device for positioning a joint, includes a patient support having a substantially flat surface. The patient support can be configured to be positioned proximate to a chair. The joint positioning device can further include a shoulder pole mounted to the patient support. The shoulder pole can be oriented substantially perpendicular to the substantially flat surface of the patient support. The joint positioning device can also further include a cylindrical shoulder pad mounted to the shoulder pole. The shoulder pad can be oriented substantially perpendicular to the shoulder pole.

In some examples, the patient support is configured such that the patient may rest on the patient support. The shoulder pad can be configured to be positioned underneath a patient's arm. The shoulder pad can be further configured to brace a patient's shoulder. The shoulder pad can be further configured to position a patient's shoulder to provide access to a glenoid cavity of the shoulder for an endoscopic procedure. In some examples, at least a portion of the patient support is configured to be positioned on a floor beneath the chair. The patient support can include a plurality of holes on a top surface of the patient support, the plurality of holes configured to receive the shoulder pole. The plurality of holes can be positioned along the length of the patient support. The shoulder pole and shoulder pad can be positionable in a hole located at one end of the patient support. The shoulder pole and shoulder pad can be positionable along a side of the chair. The patient support can be sized to counterbalance the weight of the shoulder pole and shoulder pad. The position of the shoulder pole may be adjustable along a length of the patient support. In some examples, a length of the shoulder pole is adjustable based on a height of the patient. The patient support can have a width less than the width of the chair. The shoulder pole can be a metal pole. In some examples, a stabilizer plate can be positioned perpendicular to a longitudinal axis of the patient, the stabilizer plate configured to stabilize the joint positioning device.

In some examples, a method of positioning a shoulder for an endoscopic procedure, can include providing a positioning device comprising a patient support, a shoulder pole, and a shoulder pad; positioning at least a portion of a flat surface of the patient support on a floor beneath a chair; positioning a patient to sit on the chair; adjusting the shoulder pole relative to the height of the patient seated on the chair such that the shoulder pad is positioned within an axilla of the patient; and applying pressure to the shoulder such that an axillary space of the shoulder opens.

The method can further include inserting a needle endoscope into a tissue site and collecting an image. The method can further include inserting a needle endoscope into a tissue site and performing an injection.

Additional examples of joint positioning devices and their methods of use, are described below.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

Examples disclosed in this section or elsewhere in this application relate to devices and methods for positioning joints for minimally invasive tissue visualization and access, including endoscopic procedures.

Before the present invention is described in greater detail, it is to be understood that this invention is not limited to particular examples described, as such may, of course, vary. It is also to be understood that the terminology used herein is for the purpose of describing particular examples only, and is not intended to be limiting, since the scope of the present invention will be limited only by the appended claims.

Where a range of values is provided, it is understood that each intervening value between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the terms "about," "around," and "approximately." These terms are used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual examples described and illustrated herein has discrete components and features which may be readily separated from or combined with the features of any of the other several examples without departing from the scope or spirit of the present invention. Any recited method can be carried out in the order of events recited or in any other order which is logically possible.

Figure 1A:
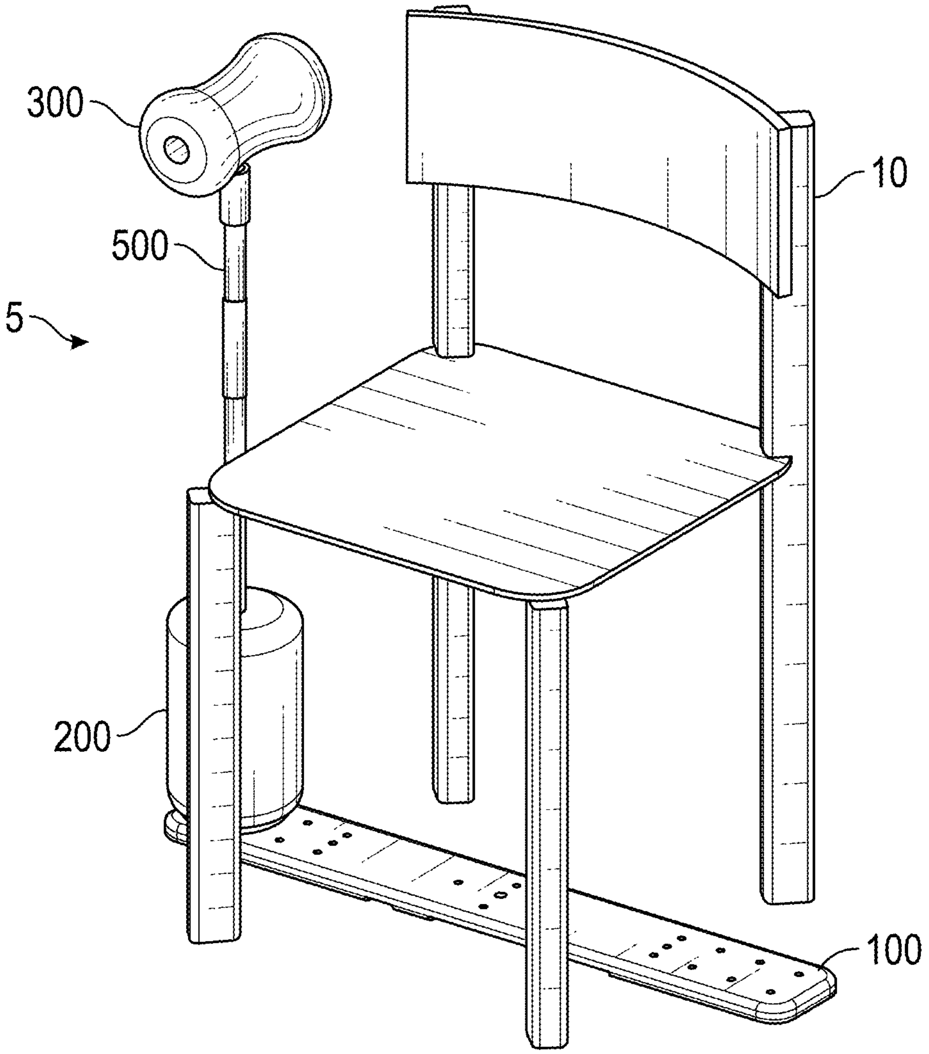
FIGS. 1A-1B illustrate an example of a joint positioning device positioned with a chair from different perspectives.
Figure 1B:
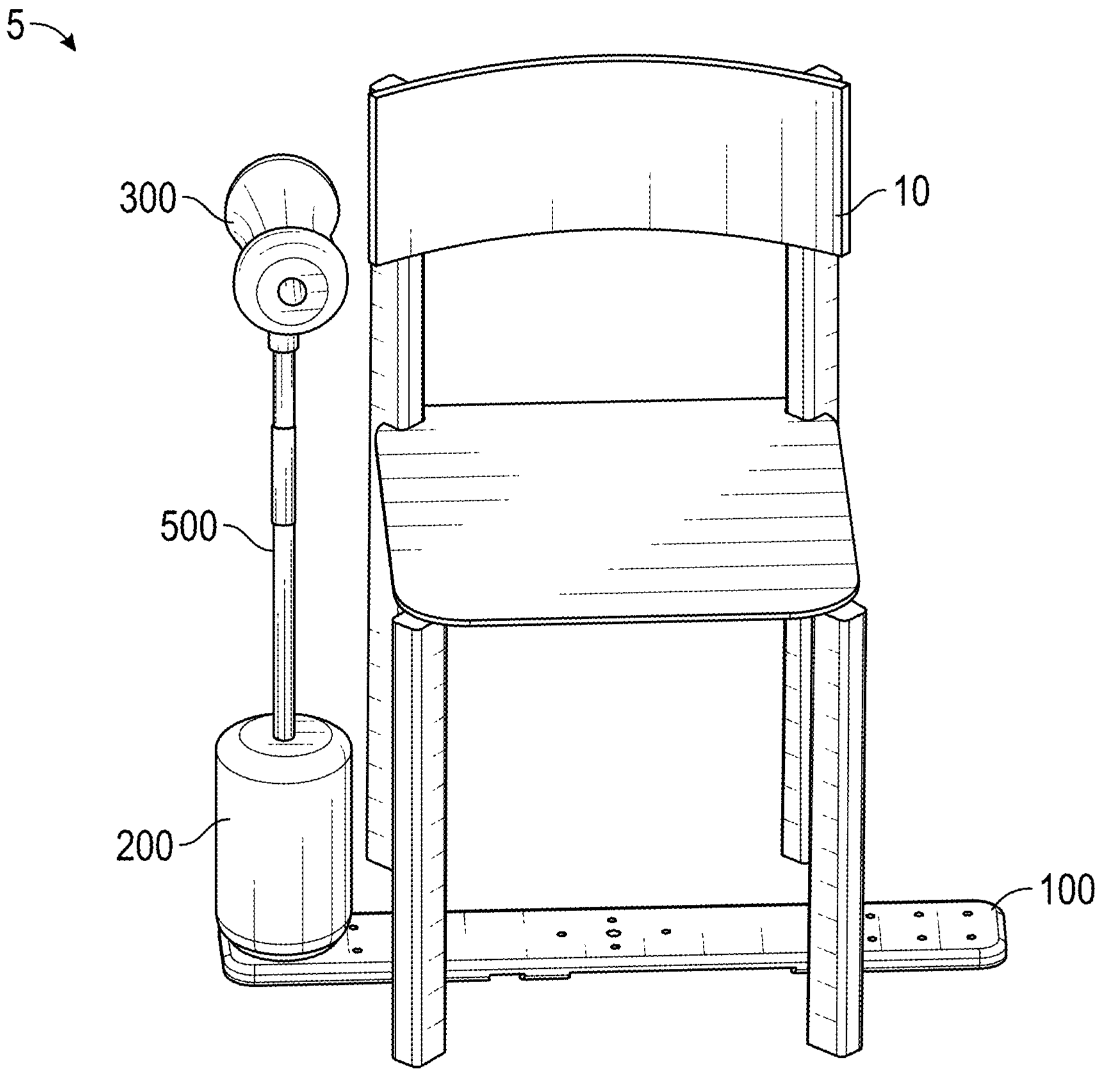

FIG. 1A illustrates a joint positioning device 5 positioned proximate to a chair 10. FIG. 1B illustrates a joint positioning device 5 positioned proximate to a chair 10 from a different perspective than FIG. 1A. The joint positioning device 5 can be adapted for proper positioning and stabilization of a shoulder joint for imaging and injection. However, the joint positioning device 5 is applicable to numerous other medical treatments of various joints. The joint positioning device 5 may also be used to access different areas or tissue sites of any particular joint, for example the shoulder. The device may be suitable for the wrist, ankle, hip, elbow, or other appropriate joints.

In some examples, the joint positioning device 5 may include a patient support 100, a vertical pillar 200, a shoulder pole 500, and a shoulder pad 300. The patient support 100 of the joint positioning device 5 may be positioned beneath the chair 10, as shown in FIGS. 1A-1B. The joint positioning device 5 may be positioned such that the shoulder pole 500 and shoulder pad 300 may be positioned on either side of the chair 10. In certain examples, the joint positioning device 5 may be engaged with the chair 10 or be attached to the chair 10 directly. The chair 10 may have a hole through the seat of the chair 10 to receive the shoulder pole 500. The hole of the chair 10 may engage with the shoulder pole 500. The joint positioning device 5 may be attached or secured to the chair 10 by other suitable means.

In some examples, the patient support 100 may be positioned anywhere beneath or alongside the chair 10. The patient support 100 may be positioned to lay flat on the surface or floor beneath the chair 10, as shown in FIG. 1A-1B. The joint positioning device 5 may be positioned near the chair 10 in other configurations, such as positioning the patient support 100 adjacent to the chair 10. The patient support 100 may be positioned in the middle of the area beneath the chair 10. The patient support 100 may be positioned partially beneath chair 10 and partially extending beyond the chair 10. The patient support 100 may be substantially positioned beneath the chair 10. The patient support 100 may be positioned towards the edge of the chair 10. The patient support 100 may be positioned alongside, behind, in front of, or anywhere near the chair 10. Once the joint positioning device 5 is positioned and placed near the chair 10, the patient may sit on the chair 10.

The patient support 100 may have a longitudinal axis and lateral axis, where the longitudinal axis and lateral axis are substantially perpendicular from each other. The longitudinal axis may be substantially parallel to the length of the patient support 100. The lateral axis may be substantially parallel to the width of the patient support 100.

The length of the patient support 100 may be substantially aligned with the width of the chair 10. The longitudinal axis of the patient support 100 may be aligned with the lateral axis or width of the chair 10. The patient support 100 may have a length longer than the width of the chair 10, such that one or more ends of the patient support 100 may extend beyond the width of the chair 10. The patient support 100 may be positioned along either side of the chair 10, such that the length of the patient support is aligned with the longitudinal axis or length of the chair 10.

In some examples, the joint positioning device 5 may be positioned on a standard medical examination table (not shown). The joint positioning device 5 may be positioned on other various types and sizes of medical examination tables, such as surgical or operating tables, bariatric tables, pediatric exam tables, or treatment tables.

The patient support 100 may be a substantially flat board or platform. The patient support 100 may be substantially rigid. The patient support 100 may be flexible. The patient support 100 may be made of plastic, metal, foam, for example closed-cell foams, or other suitable material. The metal may be stainless steel, chrome, or any suitable metal that is corrosion-resistant and readily cleanable.

The patient support 100 may be substantially rectangular, as shown in FIGS. 1A-1B. The patient support 100 may be elongated, extending along a longitudinal axis. The patient support 100 may be adjustable such that the length or width may be adjusted. The patient support 100 may be dimensioned or sized to counterbalance the shoulder pole 500 and shoulder pad 300 to stabilize the joint positioning device 5. The patient support 100 may also have a minimum weight sufficient to counterbalance the shoulder pole 500 and shoulder pad 300 to stabilize the joint positioning device 5.

While the dimensions of the patient support 100 may vary, the length of the patient support 100 ranges from about 10 inches to about 100 inches, such as about 59.5 inches to about 75.5 inches, including about 20 inches to about 60 inches. For example, 26 inches or 33 inches. While the dimensions of the patient support 100 may vary, the width of the patient support 100 ranges from 1 inch to 30 inches, including 2 inches to 20 inches, and including 3 inches to 5 inches. While the dimensions of the patient support 100 may vary, the thickness or height of the patient support 100 ranges from 0.1 inches to 5 inches, such as 0.3 inches to 3 inches, including 0.5 inches to 1.5 inches. The dimensions of the chair may vary depending on the size of the patient.

The shoulder pole 500 can be telescoping such the height of the shoulder pole 500 can be raised or lowered. The length or height of the shoulder pole 500 can be adjusted depending on the patient's size or orientation. The shoulder pole 500 may have an adjustable height that can be adjusted by loosening a collar, extending the pole and then tightening the collar, to optimize the position of the shoulder pad 300 and the patient's shoulder for access and visualization for an endoscopic procedure.

While the dimensions of the shoulder pole 500 may vary, the length or height of the shoulder pole 500 ranges from 20 inches to 80 inches, such as 25 inches to 70 inches, including 30 inches to 60 inches. While the dimensions of the shoulder pole 500 may vary, the diameter of the shoulder pole 500 ranges from 0.2 inches to 5 inches, such as 0.3 inches to 3 inches, including 0.5 inch to 1.5 inches.

The shoulder pad 300 may mount to the shoulder pole 500. The shoulder pad 300 may be oriented such that the length of the shoulder pad 300 may be substantially perpendicular to the length of the shoulder pole 500. The length of the shoulder pad 300 may be aligned with the width of the patient support 100. The shoulder pad 300 may be oriented such that the length of the shoulder pad 300 may be substantially parallel to the length of the patient support 100. The shoulder pad 300 may adjustable to turn or rotate to adjust the orientation of the shoulder pad 300. The shoulder pad 300 may be adjustable similar to the height of the shoulder pole and may be adjustable using the same collar or a separate collar. The shoulder pad 300 can be adjusted by loosening the collar, rotating or spinning the shoulder pad 300 and then tightening the collar to lock the shoulder pad 300 in the desired position, such as aligned with the patient's arm pit.

In some examples, the shoulder pad 300 may be rotated relative to the shoulder pole 500 and/or the patient support 100. The shoulder pad 300 may be rotated such that the longitudinal axis or length of the shoulder pad 300 may be aligned along different axes, for example, aligned with the length of the seat of the chair 10 or with the sagittal axis of the patient's torso when seated on the chair 10. The shoulder pad 300 may be positioned or rotated to correctly position the patient's arm and shoulder.

While the dimensions of the shoulder pad 300 may vary, the length the shoulder pad 300 ranges from 4 inches to 12 inches, such as 5 inches to 10 inches, including 6 inches to 8 inches. While the dimensions of the shoulder pad 300 may vary, the diameter of the should pad 300 ranges from 0.5 inches to 5 inches, such as 1.0 inches to 3 inches, including 1.0 inch to 1.5 inches. In examples, the shoulder pad 300 may be generally cylindrical with end portions having a diameter that is greater than a center portion of the shoulder pad 300, such that the shoulder pad is ergonomically favorable for a patient to rest an arm over the should pad while seated in the chair 10. The shoulder pad may have an internal hole, extending along a longitudinal axis along the entire length of the shoulder pad or part of the entire length of the shoulder pad.

Figure 2A:
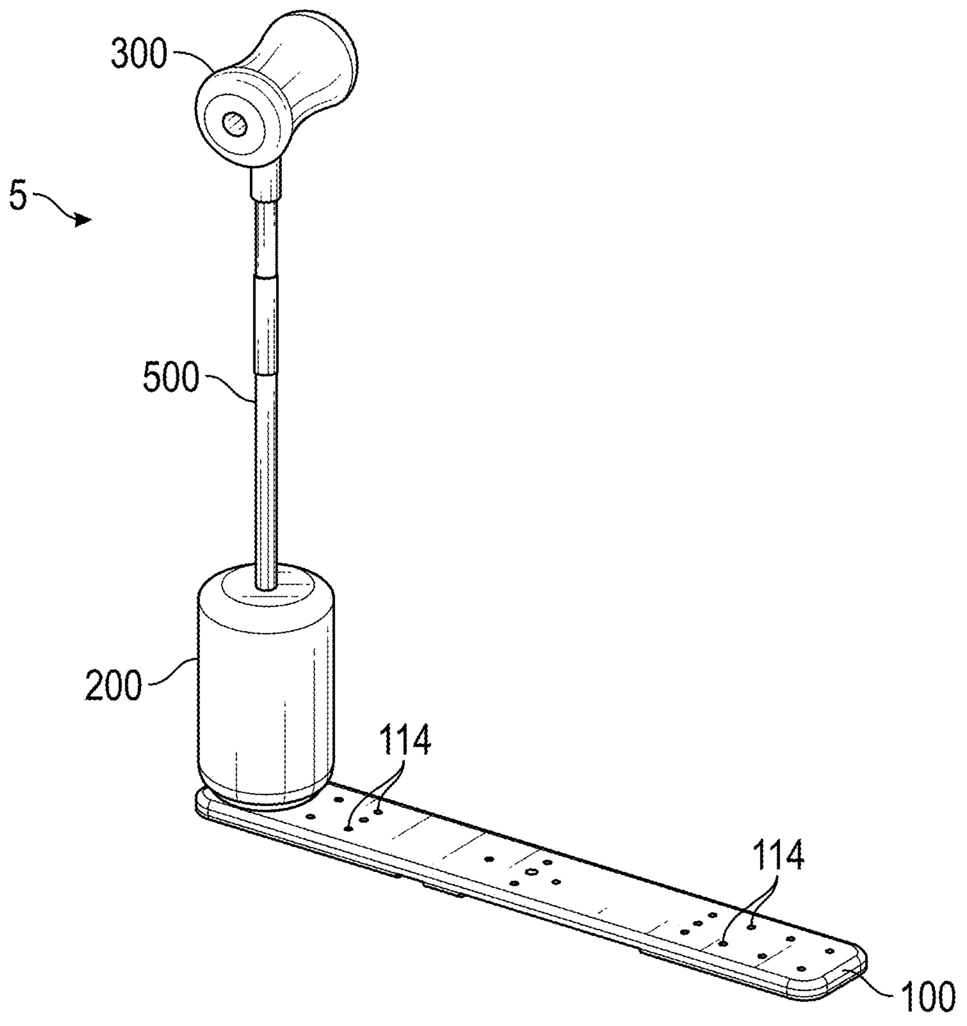
FIGS. 2A-2E illustrate an example of a joint positioning device.
Figure 2B:
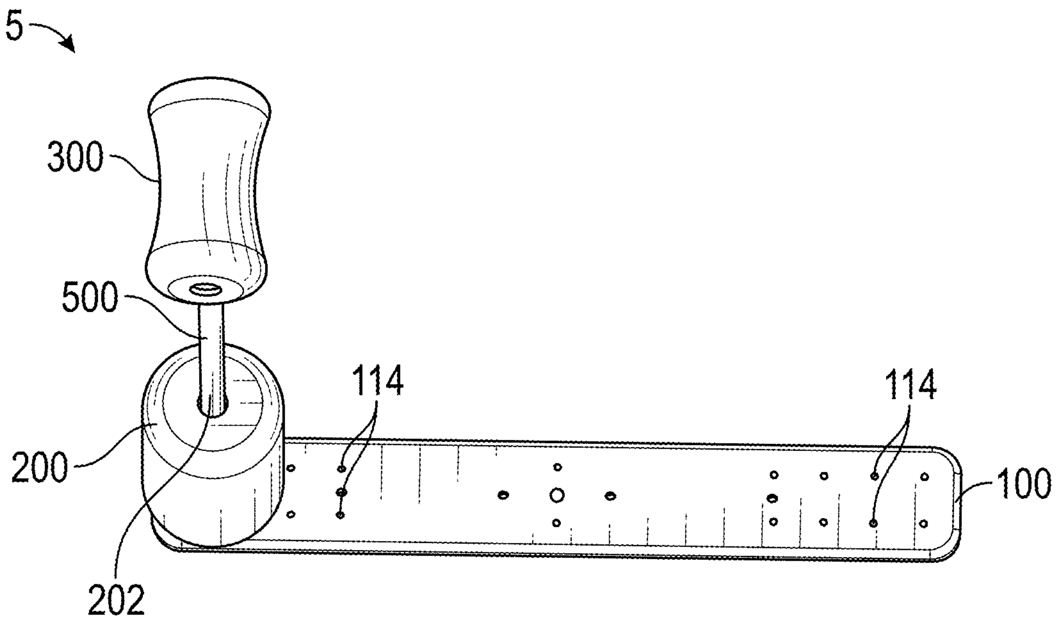
Figure 2C:
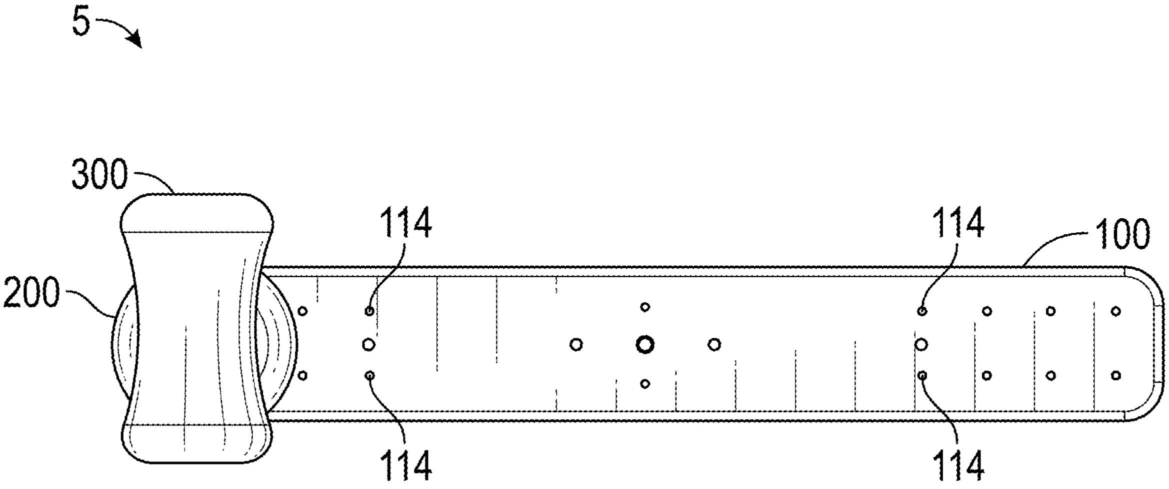
Figure 2D:
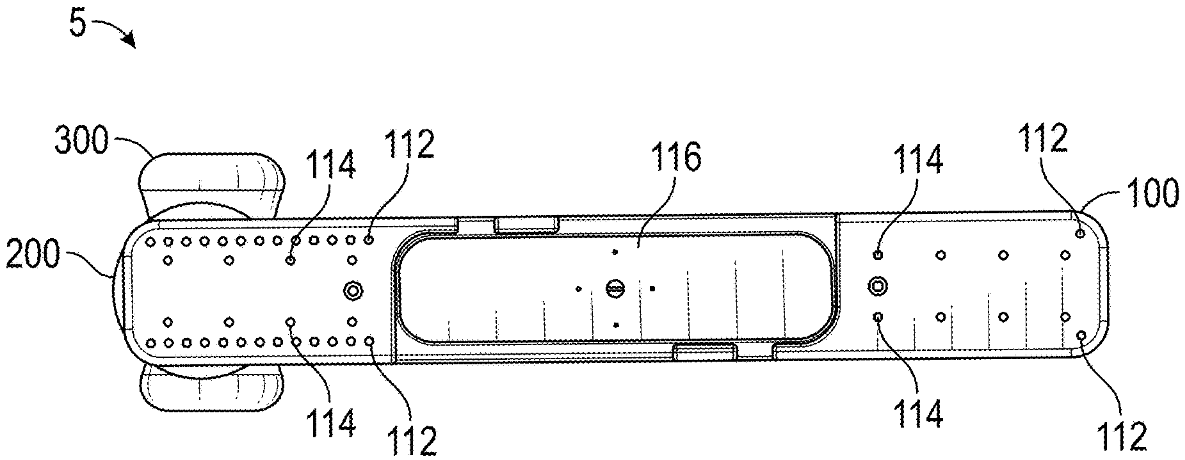
Figure 2E:
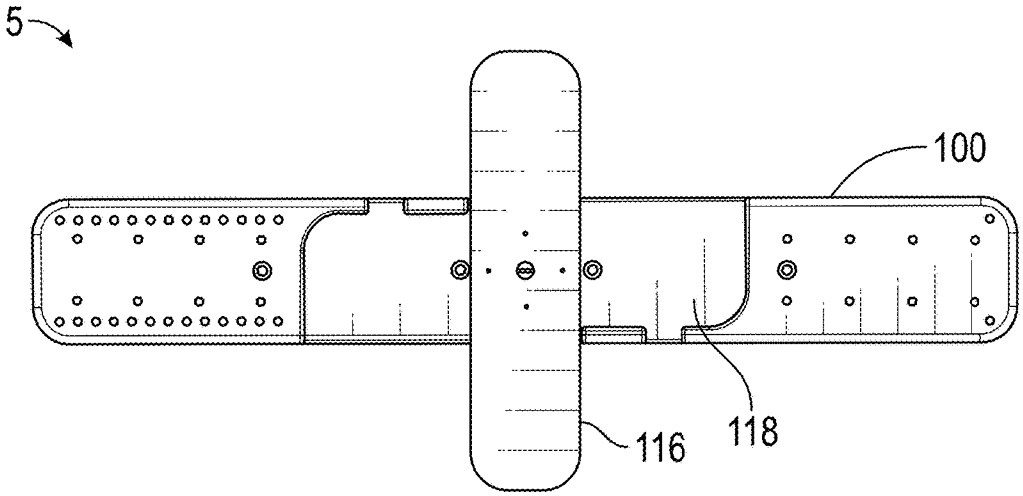
Figure 3:
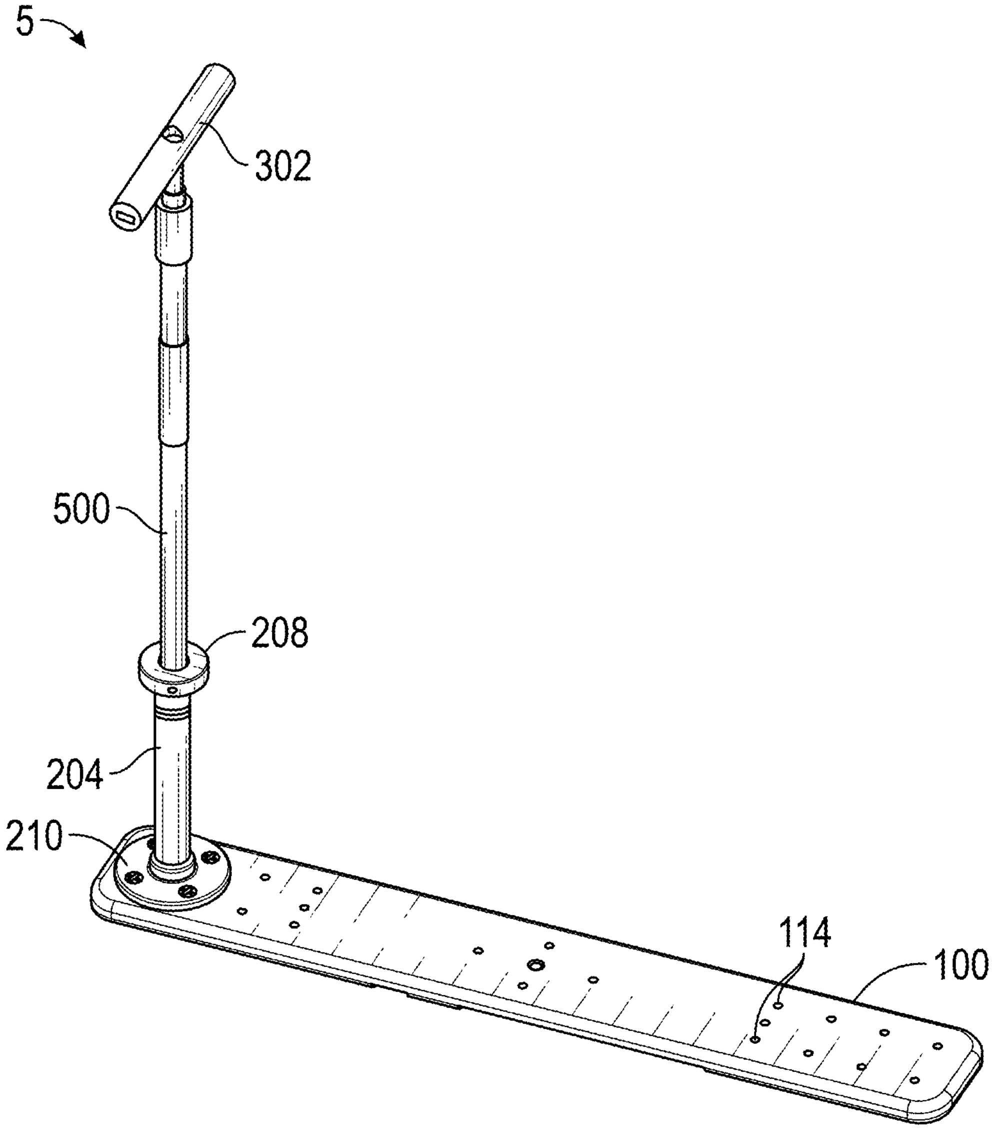
FIG. 3 illustrates an example of a joint positioning device with the vertical pillar padding removed.

Turning to FIGS. 2A-3, in certain examples, the joint positioning device 5 includes a vertical pillar 200 that extends from the substantially flat surface of the patient support 100. As shown in FIG. 3, the vertical pillar 200 may include a pole 204. The pole 204 of the vertical pillar 200 may include a central hole or aperture 202. The shoulder pole 500 may be positioned within the central hole or aperture 202 of the pole 204. The shoulder pole 500 can be received by the hole or aperture 202 of the pole 204, such that the shoulder pole 500 may extend vertically from the vertical pillar 200.

The patient support 100 may have a series of holes 114, as shown in FIGS. 2A-2E. The holes 114 may secure the base 210 as will be described more below. The base 210 can be used to secure the pole 204 and/or the shoulder pole 500. In some examples, the holes 114 may also receive the pole 204 or the shoulder pole 500. The holes 114 may be threaded or otherwise structured to engage and secure the pole 204 or the shoulder pole 500. One skilled in the art will understand that the pole 204 or shoulder pole 500 may be secured into base via any suitable means disclosed herein this section or elsewhere in the specification. For example, the pole 204 or shoulder pole 500 may be secured via press-fit and/or via bayonet attachment.

Although the series of holes 114 shown in FIGS. 2A-2E are positioned on the proximal and distal ends of the patient support 100, the series of holes 114 may be positioned anywhere along the length of the patient support 100. The series of holes 114 may be positioned along the entire length of the patient support 100. The series of holes 114 allows for the pole 204 or shoulder pole 500 to be adjusted and positioned along the length of the patient support 100.

As shown in FIG. 2D, the patient support 100 may be adjustable such that the length or width may be adjusted. The proximal and distal ends of the patient support 100 may be shifted along the longitudinal axis to expand or shorten the length of the patient support 100. A stabilizer arm or plate 116 may be placed within a recess between the proximal and distal ends of the patient support 100. The longitudinal axis or length of the stabilizer arm or plate 116 may be aligned with the longitudinal axis or length of the patient support 100. The stabilizer arm or plate 116 can rotate to be perpendicular to a longitudinal axis or length of the patient support 100. The stabilizer plate 116 may be used in various positions to stabilize and counterbalance the pillar 200, the shoulder pole 500, and/or the shoulder pad 300.

The patient support 100 may have a substantial height or thickness counterbalance the weight of the shoulder pole 500 and shoulder pad 300 as well as any pressure applied by a patient or doctor. The patient support 100 may have a height or thickness that is optimized to stabilize the joint positioning device 5, even when pressure or weight is applied to the joint positioning device 5.

FIG. 2E illustrates a bottom view of an example of the joint positioning device 5, shown without the shoulder pole 500 or shoulder pad 300, showing a stabilizer plate 116. A stabilizer plate 116 may be placed within a recess 118 between the proximal and distal ends of the patient support 100. The longitudinal axis or length of the stabilizer plate 116 may be aligned with the longitudinal axis or length of the patient support 100. The stabilizer plate 116 can rotate to be perpendicular to a longitudinal axis or length of the patient support 100 as shown in FIG. 2E. The stabilizer plate 116 may be used in various positions to stabilize and counterbalance the pillar 200 and/or the shoulder pole 500.

Vertical Pillar

Also shown in FIGS. 2A-2D, the joint positioning device 5 includes a vertical pillar 200 that extends substantially perpendicular from the substantially flat surface of the patient support 100. The vertical pillar 200 extends substantially perpendicular from the substantially flat surface of the patient support 100.

The vertical pillar 200 may be positioned at the end of the patient support 100, as shown in FIGS. 2A-2D. The vertical pillar 200 may be positioned at either end of the patient support 100, such as the proximal or distal end of the patient support 100. The vertical pillar 200 may be positioned anywhere along the length and/or width of the patient support 100. The vertical pillar 200 may be padded. The vertical pillar 200 may include a pole 204 with padding or a padded surface. The padding or padded surface may be made of foam, felt, or any other suitable material. The padding of the vertical pillar 200 may be round. The padding of the vertical pillar 200 may have variety of shapes, such as contoured round pincushion (vertical lines go toward center), contoured round barrel (vertical lines go away from center), rectangular or square, or any other suitable shape.

FIG. 3 illustrates a joint positioning device 5 with the padding of the vertical pillar 200 removed.

Figure 5:
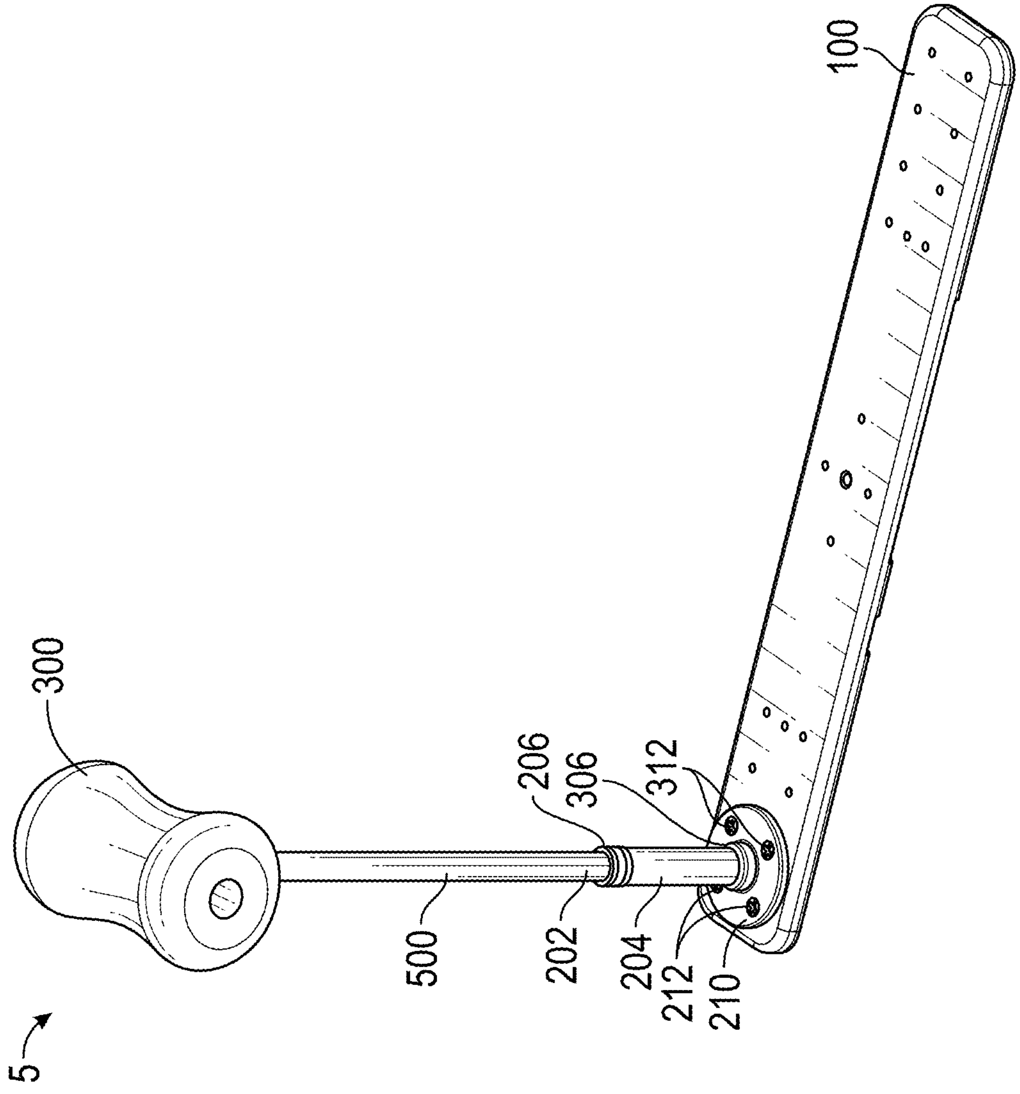
FIG. 5 illustrates an example of a joint positioning device with the outer padding of the vertical pillar removed.

FIG. 5 illustrates the joint positioning device 5 with the pole 204 of the vertical pillar 200 without the padding and with the shoulder pole 500 with a shoulder pad 300.

As shown in FIG. 3, the joint positioning device 5 may include a support 208. The support 208 may be used to set the height and also secure the pole 204 and the shoulder pole 500. The support 208 can further be used to secure the padding of the vertical pillar 200 to prevent the padding from shifting from the pole 204.

FIGS. 3 and 5 illustrates the vertical pillar 200 without the padding or a padded surface. The vertical pillar 200 may be a pole 204 without padding. The pole 204 may be made of metal, plastic, or any other suitable material.

While the dimensions of the pole 204 may vary, the height of the pole 204 ranges from 4 inches to 30 inches, such as 5 inches to 15 inches, including 6 inches to 10 inches. While the dimensions of the pole 204 may vary, the diameter of the pole 204 ranges from 0.3 inches to 6 inches, such as 0.5 inches to 3 inches, including 0.7 inch to 1.5 inches.

The joint positioning device 5 may include a base 210. The base 210 may include a central hole or aperture 306 to receive the pole 204. While the dimensions of the base 210 may vary, the diameter of the base 210 ranges from 1 inches to 15 inches, such as 2 inches to 10 inches, including 3 inches to 5 inches.

The pole 204 may include a central hole or aperture 202. The ends 206 of the pole 204 may be threaded or otherwise structured to engage and secure the pole 204 to the base 210. The ends 206 of the pole 204 may be threaded or otherwise structured to engage center hole or aperture 306 of the base 210. The center hole or aperture 306 of the base 210 may have corresponding threading or structure to engage with the threads of the ends 206 of the pole 204. One of skill in the art will understand that the pole 204 may be secured into base 210 via any suitable means disclosed herein this section or elsewhere in the specification. For example, the pole 204 may be secured via press-fit and/or via bayonet attachment.

As described above, the patient support 100 may include a series of holes 114 may be threaded or otherwise structured to engage with and secure the pole 204 to the patient support 100. The screws 312 may be inserted through the base 210 and into the patient support 100. The base 210 may include a series of holes or apertures 212 configured to receive screws 312. The screws 312 may be used to secure the base 210 to the patient support 100. The central hole 306 of the base 210 may receive the pole 204.

The pole 204 may be attached or secured to the patient support 100 in a number of ways. The pole 204 may be integral with the patient support 100. The pole 204 may attach directly to the patient support 100 without the base 210. For example, the patient support 100 may have a series of holes 114 dimensioned to receive the pole 204. The pole 204 may have threads or be structured to engage with holes 114 of the patient support 100.

While the dimensions of the vertical pillar 200 may vary, the height of the vertical pillar 200 ranges from 4 inches to 30 inches, such as 5 inches to 15 inches, including 6 inches to 10 inches. While the dimensions of the vertical pillar 200 may vary, the diameter of the vertical pillar 200 ranges from 2 inches to 12 inches, such as 4 inches to 10 inches, including 5 inches to 6 inches.

Shoulder Pole and Pad

FIG. 3 illustrates the shoulder pad 300 with the outer padding removed. The shoulder pad 300 may include a horizontal pole 302 is covered with the outer padding (not shown in FIG. 3). The length of the horizontal pole 302 may be substantially perpendicular to the shoulder pole 500. The horizontal pole 302 may have an aperture or hole to receive the shoulder pole 500. The end 506 of the shoulder pole 500 may be inserted into the hole of the horizontal pole 302. The horizontal pole 302 may be covered with the shoulder pad 300.

Figure 4:
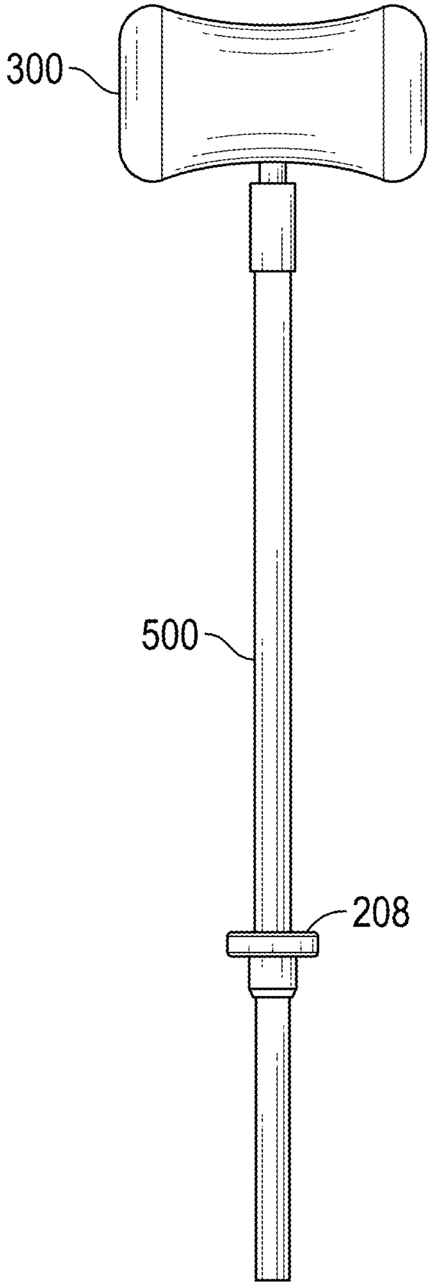
FIG. 4 illustrates a close-up view of an example of a shoulder pole and shoulder pad of a joint positioning device.

FIG. 4 illustrates a close up view of the shoulder pole 500 and shoulder pad 300 without the patient support 100.

FIG. 5 illustrates the joint positioning device 5 with the pole 204 of the vertical pole 204 without the padding and with the shoulder pole 500 with a shoulder pad 300.

The shoulder pad 300 may be substantially cylindrical. The shoulder pad 300 may be contoured round pincushion (vertical lines go toward center) as shown in FIGS. 2A-2D. The shoulder pad 300 may have a diameter that narrows towards the middle but increases towards each end. The shoulder pad 300 may have variety of shapes, such as contoured round pincushion (vertical lines go toward center), contoured round barrel (vertical lines go away from center), rectangular or square, or any other suitable shape.

The shoulder pole 500 may be secured to the patient support 100 in several ways. The shoulder pole 500 may be integral with the patient support 100. As shown in FIGS. 3 and 5, the shoulder pole 500 may be inserted into the hole or aperture 202 of the pole 204. The hole or aperture 202 of the pole 204 may be structured to engaged with and secure the shoulder pole 500. The shoulder pole 500 may attach to the patient support 100 itself. As described herein, the patient support 100 may have holes 114 dimensioned to receive the shoulder pole 500. The end of the shoulder pole 500 may have threads or be structured to engage with the holes 114 of the patient support 100.

Figure 6:
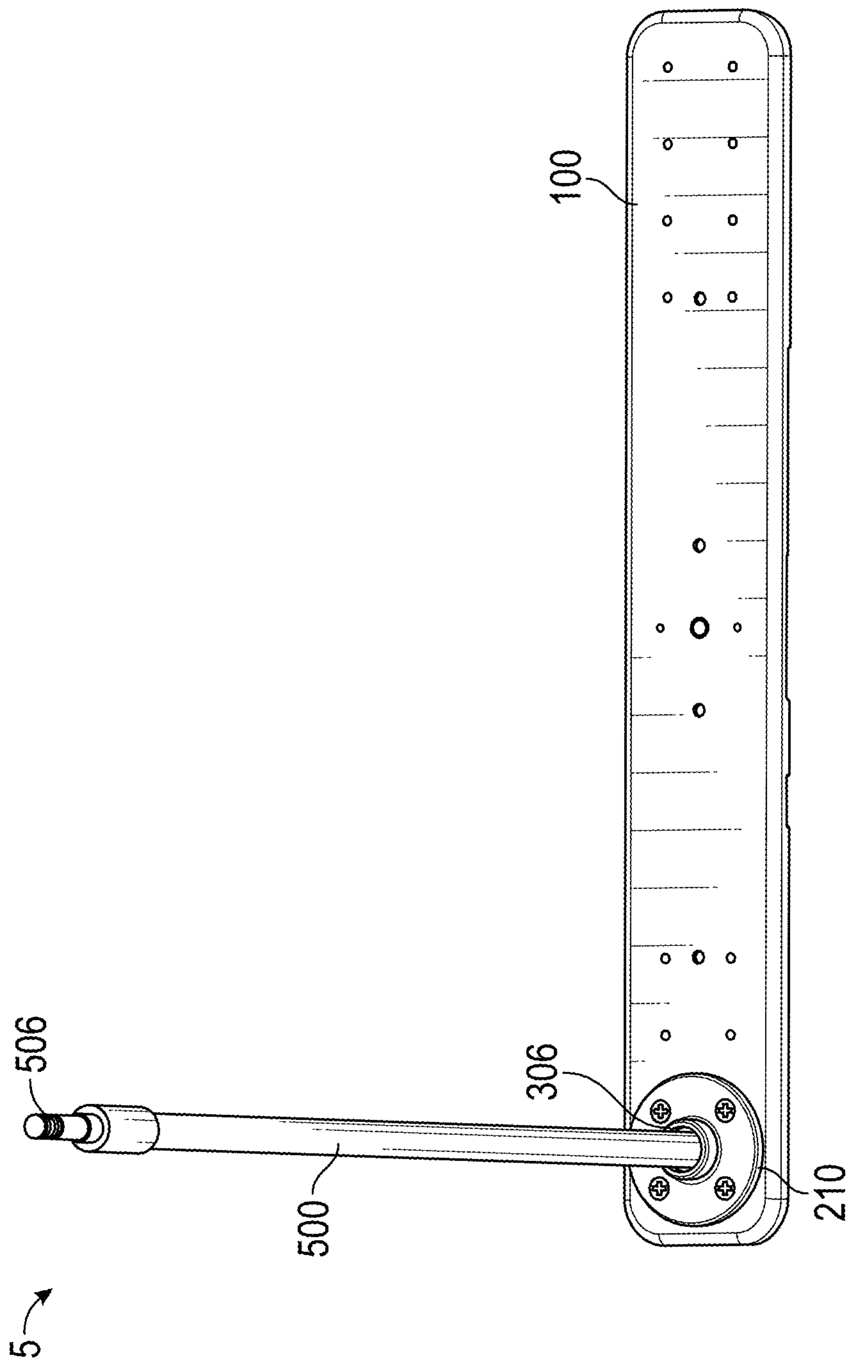
FIG. 6 illustrates an example of a joint positioning device with the vertical pillar removed.

FIG. 6 illustrates the joint positioning device 5 without the vertical pillar 200 and without the shoulder pad 300. As shown in FIG. 6, the shoulder pole 500 may be secured to the patient support 100 with a base 210. The center hole 306 of the base 210 may receive and engage with the end of the shoulder pole 500, without the presence of the vertical pole 204. As described herein, the screws or pegs 312 may be inserted through the base 210 and into the patient support 100. The base 210 may include a series of holes or apertures 212 configured to receive screws or pegs 312. The screws or pegs 312 may be used to secure the base 210 to the patient support 100. The central hole 306 of the base 210 may receive the shoulder pole 500. The central hole 306 may be threaded or configured to engage with the shoulder pole 500. The shoulder pole 500 may have corresponding threads or structure to engage with the threads or structure of the hole or aperture 306 of the base 210.

Figure 7:
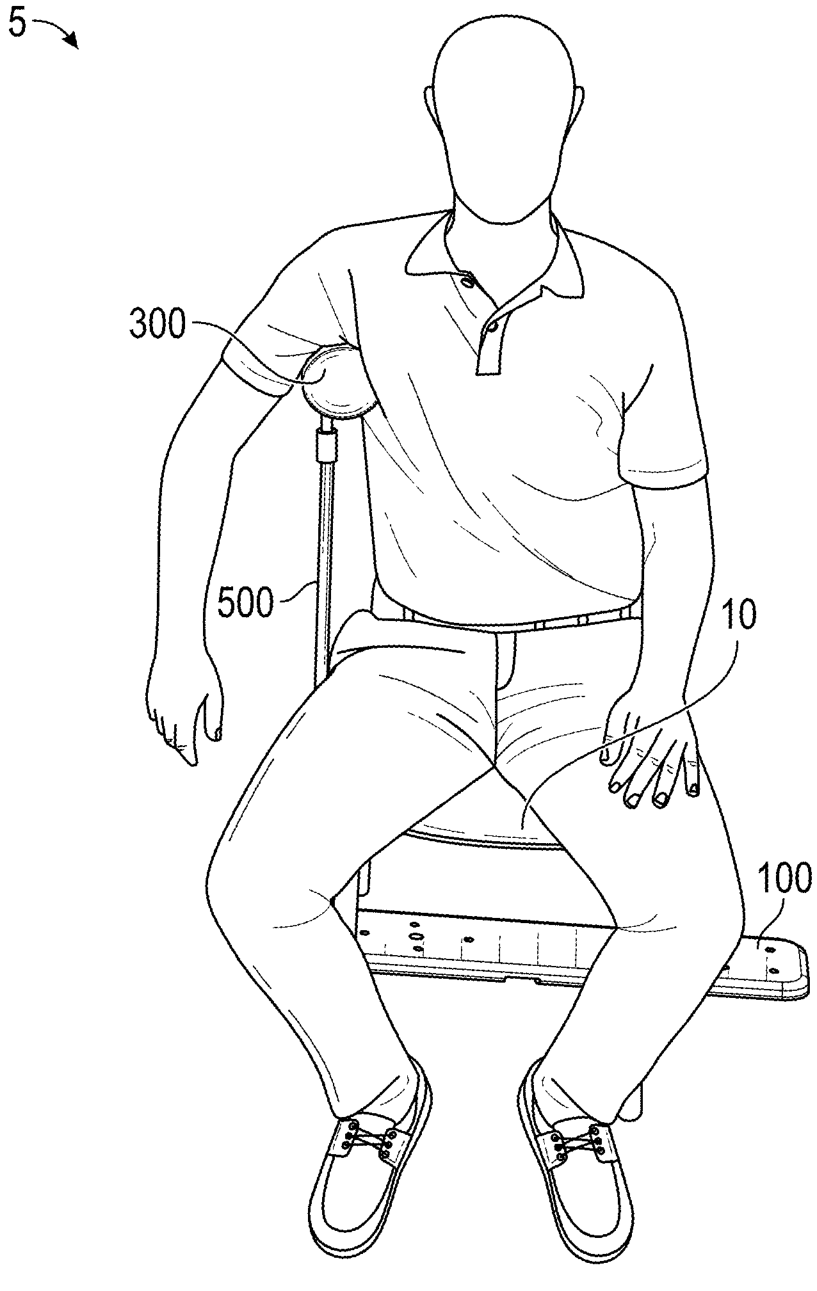
FIG. 7 illustrates an example of a patient positioned on a chair with a joint positioning device.

FIG. 7 illustrates a patient positioned on a joint positioning device 5. Once the joint positioning device 5 is positioned near the chair 10, the patient may sit on the chair 10. The patient may sit on the chair 10 such that the shoulder pole 500 and shoulder pad 300 is immediately adjacent to or next to patient's side, as illustrated in FIG. 7.

As described herein, the shoulder pole 500 can be telescoping such the height of the shoulder pole 500 can be raised or lowered. The length or height of the shoulder pole 500 can be adjusted depending on the patient's size or orientation. The shoulder pole 500 may have an adjustable height that can be adjusted to optimize the position of the shoulder pad 300 and the patient's shoulder for access and visualization for an endoscopic procedure. As described herein, the shoulder pad 300 may be rotated to different orientations, depending on the position of the patient and/or the patient support 100.

The patient's arm may be positioned over the shoulder pad 300 such that the shoulder pad 300 is positioned underneath the patient's arm, in the patient's armpit or axillary. The patient's shoulder of interest may be braced against the shoulder pad 300. Once the patient's shoulder is braced against the shoulder pad 300, a physician may press, push, or apply pressure to the patient's shoulder or arm to position the patient. The patient may hold a weight in their hand to further provide traction and pressure to open the shoulder joint and provide access to the glenoid cavity.

The physician may appropriately adjust the patient, shoulder pad 300, and shoulder pole 500, and/or the patient support 100 such that the patient's shoulder is braced in the correct position. The physician may position or place the patient's shoulder in an outward position to open up the glenoid cavity of the patient's shoulder. The physician may apply pressure to the shoulder such that the glenoid cavity of the shoulder becomes open. Once the patient is in the correct position, the glenoid cavity of the shoulder of interest is accessible. While the patient's shoulder and arm is being rotated or extended outward, the patient's upper body remains stabilized to put a slight torque or force on the patient's shoulder.

The patient may be positioned on either side of the shoulder pad 300 and shoulder pole 500 to allow for access of either shoulder or arm of the patient.

Once the glenoid cavity of the patient's shoulder is in an open position, the physician may then have the necessary access and visualization of the glenoid cavity of the patient's shoulder to examine the internal tissue of the shoulder, such as via a needle endoscope. The physician may insert a needle endoscope into a tissue site and collect an image. Additionally, once the glenoid cavity of the patient's shoulder is accessible, the physician may and perform any necessary procedures or treatments such as an injection. The physician may then inject the patient's joint, such as via a needle endoscope, with access to the glenoid cavity of the shoulder.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing examples. The protection extends to any novel one, or any novel combination, of the features disclosed in this specification (including any accompanying claims, abstract and drawings), or to any novel one, or any novel combination, of the steps of any method or process so disclosed.

While certain examples have been described, these examples have been presented by way of example only, and are not intended to limit the scope of protection. Indeed, the novel methods and systems described in this section or elsewhere in this specification may be embodied in a variety of other forms. Furthermore, various omissions, substitutions and changes in the form of the methods and systems described in this section or elsewhere in this specification may be made. Those skilled in the art will appreciate that in some examples, the actual steps taken in the processes illustrated and/or disclosed may differ from those shown in the figures. Depending on the example, certain of the steps described above may be removed, others may be added. Furthermore, the features and attributes of the specific examples disclosed above may be combined in different ways to form additional examples, all of which fall within the scope of the present disclosure.

Although the present disclosure includes certain examples and applications, it will be understood by those skilled in the art that the present disclosure extends beyond the specifically disclosed examples to other alternative examples and/or uses and obvious modifications and equivalents thereof, including examples which do not provide all of the features and advantages set forth in this section or elsewhere in this specification. Accordingly, the scope of the present disclosure is not intended to be limited by the specific disclosures of preferred examples in this section or elsewhere in this specification, and may be defined by claims as presented in this section or elsewhere in this specification or as presented in the future.

What is claimed is:

1. A method of positioning a shoulder for an endoscopic procedure, the method comprising:

providing a positioning device comprising a patient support, a shoulder pole, and a shoulder pad, wherein the patient support is configured to counterbalance the weight of the shoulder pole and shoulder pad;

positioning at least a portion of an elongated flat surface of the patient support on a floor beneath a chair;

positioning a patient to sit on the chair such that the elongated flat surface extends under the patient;

adjusting the shoulder pole relative to a height of the patient seated on the chair such that the shoulder pad is positioned within an axilla of the patient; and applying pressure to the shoulder such that an axillary space of the shoulder opens.

2. The method of claim 1, further comprising resting the patient on the patient support.

3. The method of claim 1, further comprising bracing the shoulder of the patient against the shoulder pad.

4. The method of claim 1, wherein the patient support comprises a plurality of holes on a top surface of the patient support, the plurality of holes configured to receive the shoulder pole.

5. The method of claim 4, wherein the plurality of holes are positioned along a length of the patient support.

6. The method joint of claim 1, further comprising positioning the shoulder pole with the shoulder pad in a hole located at one end of the patient support, wherein the shoulder pole is positionable along a side of the chair.

7. The method of claim 1, wherein a position of the shoulder pole is adjustable along a length of the patient support.

8. The method of claim 1, wherein the patient support has a width less than a width of the chair.

9. The method of claim 1, wherein the shoulder pole comprises a metal pole.

10. The method of claim 1, further comprising a stabilizer plate positioned perpendicular to a longitudinal axis of the patient support, the stabilizer plate configured to stabilize the joint positioning device.

11. The method of claim 1, further comprising inserting a needle endoscope into a tissue site and collecting an image.

12. The method of claim 1, further comprising inserting a needle endoscope into a tissue site and performing an injection.

* * * * *